United States Patent [19]

Haas et al.

[11] Patent Number: 5,284,979
[45] Date of Patent: Feb. 8, 1994

[54] PROCESS FOR THE PREPARTION OF 3-HYDROXYALKANALS

[75] Inventors: Thomas Haas, Main; Georg Böhme, Rodenbach; Dietrich Arntz, Oberursel, all of Fed. Rep. of Germany

[73] Assignee: Degussa Aktiengesellschaft, Frankfurt am Main, Fed. Rep. of Germany

[21] Appl. No.: 980,955

[22] Filed: Nov. 24, 1992

[30] Foreign Application Priority Data

Nov. 27, 1991 [DE] Fed. Rep. of Germany ....... 4138981

[51] Int. Cl.$^5$ ..................... C07C 45/61; C07C 45/64
[52] U.S. Cl. .................... 568/491; 568/895; 568/496
[58] Field of Search ............... 568/496, 491, 467, 862, 568/485, 491, 496, 862, 467, 459, 895

[56] References Cited

U.S. PATENT DOCUMENTS 3,833,659  9/1974  Schmerling et al. ............... 568/491
4,709,098 11/1987  Dolifini et al. ..................... 568/491
5,015,789  5/1991  Arntz et al. ........................ 568/862

FOREIGN PATENT DOCUMENTS 922166  1/1955  Fed. Rep. of Germany ...... 568/491

*Primary Examiner*—Werren B. Lone
*Attorney, Agent, or Firm*—Beveridge, DeGrandi, Weilacher & Young

[57] ABSTRACT

A process is disclosed for the preparation of 3-hydroxyalkanals having 3 to 12 carbon atoms, in particular 3 or 4 carbon atoms, by hydration of the underlying 2-alkenals with water in a homogeneous phase in the presence of an acid catalyst. The previously known hydration using mineral acids or carboxylic acids as catalyst results in low volume/time yields and/or low selectivities. These disadvantages can be avoided by using in the present invention, as catalyst, a dissolved acid-base buffer which results in a pH of from 2 to 5 in the reaction mixture; the acid component and corresponding base of which are present in a total quantity of from 0.5 to 40% by weight in the reaction mixture. The preferred buffers composed of a lower monobasic carboxylic acid and a tertiary amine can easily be recycled.

15 Claims, No Drawings

PROCESS FOR THE PREPARTION OF 3-HYDROXYALKANALS

BACKGROUND AND INTRODUCTION

The present invention relates to a process for the preparation of 3-hydroxyalkanals having 3 to 12 carbon atoms, in particular 3 or 4 carbon atoms, by hydration of the underlying 2-alkenals with water in a homogenous phase in the presence of an acid catalyst.

2-Alkenals of the general formula $H_2C=CR-CHO$ in which R stands for hydrogen or alkyl, in particular acrolein and methacrolein, may be hydrated with water in the presence of acid catalysts (according to U.S. Pat. Nop. 2,434,110) to form the corresponding 3-hydroxyalkanals. 3-Hydroxypropionaldehyde (HPA) is obtainable from acrolein and may in turn be hydrogenated to produce 1,3-propanediol which is becoming increasingly important as monomer unit for polyesters and polyurethanes.

In the process according to U.S. Pat. No. 2,434,110, acids homogeneously dissolved in the reaction mixture, such as sulfuric acid, hydrochloric acid, phosphoric acid, oxalic acid, acid salts or acetic acid, are used as catalysts. Sulfuric acid was found to be the preferred catalyst in the prior art. The disadvantage of this process lies in the low yields and low selectivities.

Further processes have been developed to improve the selectivity of hydration of acrolein. Although suitable selectivities can be obtained by using carbon dioxide as catalyst (see British Patent 1,185,615), the long reaction time required considerably reduces the volume/time yield of this process.

Lastly, heterogeneous catalysts may be used, namely weakly acid ion exchangers containing carboxyl groups; see U.S. Pat. No. 3,536,763. In practice it was found that conventional ion exchangers containing carboxyl groups are limited in their activity and therefore required long reaction times. An improvement in volume/time yield combined with high selectivity was obtained by using ion exchangers containing phosphonic acid groups; see DE-OS 39 26 136.

As an alternative to using heterogeneous catalysts, there is a desire to find catalyst systems capable of operating in the homogeneous phase for hydration of the 2-alkenals with high selectivity as well as a satisfactory volume/time yield. Preferred catalyst systems should also be easily recoverable in the course of obtaining a secondary product from 3-hydroxyalkanals, such as in particular the alkane-1,3-diols obtainable from 3-hydroxyalkanals by hydrogenation. The reaction mixture from the hydration stage is normally only freed from unreacted 2-alkenal while 3-hydroxyalkanal is converted into a secondary product without being first isolated.

SUMMARY OF THE INVENTION

An object of the present invention is to provide a process for the preparation of 3-hydroxyalkanals, having 3 to 12 carbon atoms, by hydration of the corresponding 2-alkenals with water in the homogeneous phase in the presence of an acid catalyst at a reaction temperature of from 20° to 120° C., a pressure of from 1 bar to 20 bar, and an initial concentration of 2-alkenal in the reaction mixture of from 3 to 30% by weight. The catalyst used is a dissolved acid-base buffer based on tertiary amine or aromatic compounds containing N as heteroatoms and (a) a monobasic carboxylic acid and a soluble salt of this acid or (b) a polybasic carboxylic acid or phosphoric acid and a salt of these acids.

This buffer leads to a pH of from 2 to 5 in the reaction mixture and its acid components and corresponding base are present in the reaction mixture in a total quantity of from 0.5 to 40% by weight. The 2-alkenals are preferably acrolein or methacrolein, most preferably acrolein.

DETAILED DESCRIPTION OF THE INVENTION

Acid-base buffers which can be isolated in the course of recovering a secondary product of the 3-hydroxyalkanal are based on a monobasic carboxylic acid having a boiling point under normal pressure below 200° C., preferably below 160° C., and a salt thereof with a tertiary amine or N-heteroaromatic compound, the tertiary amine or the N-heteroaromatic compound having a boiling point under normal pressure below 200° C., preferably below 160°.

The acid-base buffers mentioned above do not produce incrustations on equipment used in distillation processes and can be separated from the reaction mixture by distillation because the salt and its components are in equilibrium:

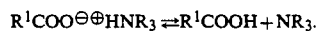

When choosing the acid and the amine, the person skilled in the art would select such combinations which can easily be decomposed by heat and have boiling points sufficiently far removed from that of the desired secondary product of the 3-hydroxyalkanal so that this secondary product can be obtained in the pure form. Particularly preferred buffer systems contain acetic acid or propionic acid as the acid component and trimethylamine, triethylamine, tripropylamine or pyridine as the tertiary amine or N-heterocyclic compound.

For example, in the case of hydration of acrolein and hydrogenation of the resulting 3-hydroxypropionaldehyde to form 1,3-propanediol, acrylic acid may also advantageously be used as the acid component of the buffer. This has the advantage that crude acrolein obtained by propene oxidation, which contains acrylic acid as by-product, may be used for the hydration stage. If separation of the acrylic acid is required, this is then only carried out after the hydration of acrolein. It is therefore not necessary to use a foreign acid component.

Suitable bases for the preparation of the buffer system (a) include not only the tertiary amines and N-heterocyclic compounds already mentioned above, but also salts of carboxylic acids which are alkaline in reaction such as alkali metal and alkaline earth metal salts and hydroxides and carbonates of alkali metals and alkaline earth metals. For the hydration itself it is of minor importance whether the reaction mixture contains trialkylammonium ions, protonated N-heterocyclic compounds or alkali metal or alkaline earth metal ions. If, however, alkali metal ions and/or alkaline earth metal ions are present, salts of these ions are left in the distillation sump after separation of the 3-hydroxyalkanal and its secondary products from the reaction mixture; thus giving rise to difficulties when the distillation sump is disposed of by combustion. Secondary amines could in principle be used instead of tertiary amines for adjusting the pH of the buffer, but the selectivity of hydration is then considerably reduced.

A preferred pH range for carrying out the hydration is from 3 to 4.5, in particular from 3 to 4. It was surprisingly found that the pH alone does not provide a sufficient technical teaching for obtaining high selectivity combined with a high volume/time yield. This aim can only be achieved by also using the buffer systems disclosed. If at a given pH the acid component of the buffer is used alone instead of the buffer itself, the reaction velocity falls to values which render the economy of the process entirely questionable.

Preparation of the buffer and adjustment of the pH in the reaction mixture are carried out in the usual manner. Preferably, the desired base component, i.e. preferably a tertiary amine, is added to an aqueous solution of the selected acid component until the desired pH is obtained.

The reaction mixture is composed of an aqueous buffer solution and the 2-alkenal which is to be hydrated. The acid component of the buffer and the corresponding base, for example acrylic acid and acrylate anion, are present in the reaction mixture in a total quantity of from 0.5 to 40% by weight, preferably from 0.5 to 5% by weight. The quantity of buffer and the quantity of 2-alkenal in the reaction mixture are adjusted to one another so that the reaction mixture forms a homogeneous phase at the reaction temperature. A preferred initial concentration of 2-alkenal in the reaction mixture is from 6 to 20% by weight, in particular from 10 to 18% by weight. Hydration may be carried out within a wide temperature range, e.g. from 20° to 120° C., preferably from 50° to 90° C. Normal pressure is generally employed but a slight excess pressure is advantageously employed at temperatures in the region of, or above, the boiling point of the 2-alkenal used.

As already mentioned above, the reaction mixture obtained from hydration is in most cases directly transferred to the production of the secondary product. Unreacted 2-alkenal is first distilled from the reaction mixture and returned to the state of hydration.

The whole catalyst, amine and acid, may be distilled off with the water after hydrogenation and recycled. Alternatively, if the amine bound in the salt has a boiling point below 100° C., it may be separated by distillation immediately after hydration and returned. When propionic acid is used as acid component of the buffer, it may be partly distilled off as azeotropic mixture with $H_2O$ after hydration.

Unexpected advantages of the process according to the invention are the high selectivities combined with good volume/time yields consistently obtained, the possibility of using crude 2-alkenals (e.g. crude acrolein containing acrylic acid), and the ease of recycling the components of the buffer based on monocarboxylic acids and tertiary amines or N-heteroaromatic compounds in the course of recovering distillable secondary products, in particular 1,3-diols.

The invention will now be further illustrated with the aid of the following Examples.

EXAMPLES

Examples 1-9 and Comparison Examples 1-4

Acrolein is hydrated to 3-hydroxypropionaldehyde (HPA) under the conditions shown in the Table. The starting concentration of acrolein indicated is adjusted by the addition of acrolein to buffer solutions having the given composition. The reaction mixture obtained is stirred at the given reaction temperature for the given reaction time. The conversion of acrolein and the selectivity with respect to HPA are then determined by gas chromatography. The conditions and results of Examples 1 to 9 and Comparison Examples VB1 to VB4 are shown in the following Table.

TABLE

| | | | | | Hydration of acrolein | | | | |
|---|---|---|---|---|---|---|---|---|---|
| | Catalyst Solution | | | | Initial acrolein conc. | Tempera- | Time | Conversion | Selectivity |
| Example | Water (g) | Acid/(g) | Base/(g) | pH | (% by weight) | ture (°C.) | (h) | (%) | (%) |
| VB1 | 180 | PrS/8 | — | 2.5 | 17 | 80 | 2 | 24.5 | 52.1 |
| 1 | 180 | PrS/8 | TEA/0.85 | 4.0 | 17 | 70 | 2 | 44.1 | 85.8 |
| VB2 | 180 | PrS/0.01 | — | 4.0 | 17 | 70 | 2 | 2.0 | |
| 2 | 180 | EsS/8 | TEA/0.38 | 3.0 | 17.2 | 70 | 2 | 32.9 | 84.8 |
| 3 | 180 | EsS/8 | TEA/0.73 | 3.3 | 17.1 | 70 | 2 | 40.1 | 86.1 |
| 4 | 180 | EsS/8 | TEA/2.22 | 3.9 | 17.3 | 70 | 2 | 49.9 | 84.3 |
| 5 | 180 | EsS/8 | NL/24.4 | 4.5 | 17.7 | 70 | 2 | 57.1 | 83.2 |
| VB3 | 180 | EsS/8 | — | 2.4 | 17.0 | 70 | 2 | 16.0 | 60.2 |
| 6 | 180 | iBuS/8 | TEA/1.3 | 4.0 | 16.8 | 70 | 2 | 50.4 | 86.9 |
| 7 | 233 | AcS/1.8 | TEA/0.29 | 3.0 | 15.9 | 90 | 3 | 53.8 | 77.0 |
| 8 | 180 | $H_3PO_4$/9.4 | TEA/8.4 | 4.1 | 16.6 | 70 | 2 | 60.7 | 80.3 |
| 9 | 180 | $H_3PO_4$/9.4 | DBA/10.6 | 4.0 | 16.8 | 60 | 2 | 58.0 | 47.9 |
| VB4 | 180 | $H_3PO_4$/$2 \times 10^{-5}$ | — | 4.0 | 16.8 | 70 | 2 | <1 | |

VB = Comparison Example (State of the Art)
EsS = acetic acid
PrS = propionic acid
iBuS = isobutyric acid
AcS = acrylic acid
TEA = triethylamine
DBA = dibutylamine
NL = sodium hydroxide solution, 10%

Example 10

Complete process:

including recovery of the catalyst $RCOOH/NR_3$. 1000 g of $H_2O$, 45 g of propionic acid (PrS) and 5 g of triethylamine (TEA) were mixed together to establish a pH of about 4. 210 g of acrolein were added to this solution. The acrolein was then reacted in a reaction tube at 70° C. at an LHSV (liquid hourly space velocity) value of 0.5 $h^{-1}$.

Unreacted acrolein was then separated from the aqueous HPA solution at reduced pressure (350 mbar). Acrolein conversion was 45%, selectivity for HPA was 85%. The HPA solution (HPA concentration =8.8% by weight) was hydrogenated in a hydrogenation autoclave with gassing stirrer. The $H_2$ pressure was 135 bar, the reaction temperature 60° C. 5 g of Raney nickel were used as catalyst. The yield of 1,3-propanediol (PD) was 99.8%, based on the HPA put into the process.

After hydrogenation, water and catalyst were distilled off in a distillation column at 50 mbar of water. Almost 100% of the TEA put into the process and 97% of the propionic acid were recovered in the aqueous distillate.

The PD left in the sump of the distillation column was purified by distillation. The total yield of 1,3-propane-diol, based on the acrolein put into the process, was 83%.

Further variations and modifications of the invention will become apparent to those skilled in the art from the foregoing and are intended to be encompassed by the claims appended hereto.

German Priority Application P 41 38 981.6, filed Nov. 27, 1991, is relied n and incorporated by reference.

What is claimed is:

1. A process for the preparation of 3-hydroxyalkanals having 3 to 12 carbon atoms, said process comprising hydrating a reaction mixture containing the corresponding 2-alkenals with water in a homogenous phase in the presence of an acid catalyst at a reaction temperature of from 20° C. to 120° C., a pressure of from 1 bar to 20 bar, and an initial concentration of the 2-alkenal in said reaction mixture of from 3 to 30% by weight, wherein said catalyst is a dissolved acid-base buffer comprising (a) a monobasic carboxylic acid and a soluble salt of said monobasic carboxylic acid or (b) a polybasic carboxylic acid or phosphoric acid, and as base a salt of said acid or a tertiary amine or a N-heteroaromatic compound, resulting in a pH of from 2 to 5 in said reaction mixture, said catalyst having an acid component and a corresponding base present in said reaction mixture in a total quantity of from 0.5 to 40% by weight.

2. The process according to claim 1, wherein said acid-base buffer is a monobasic carboxylic acid having a boiling point at normal pressure below 200° C. and a salt thereof with a tertiary amine or an N-heteroaromatic compound, said tertiary amine or said N-heteroaromatic compound having a boiling point at normal pressure below 200° C., preferably below 160°.

3. The process according to claim 2, wherein said monobasic carboxylic acid and said tertiary amine or said N-heteroaromatic compound having a boiling point at normal pressure below 160° C.

4. The process according to claim 1, wherein the pH of said reaction mixture is adjusted from 3 to 4.5 with said acid-base buffer.

5. The process according to claim 1, wherein said acid component of said catalyst is acetic acid, propionic acid or acrylic acid.

6. The process according to claim 1, wherein said acid is a lower carboxylic acid and said amine is trimethylamine, triethylamine, tripropylamine or pyridine.

7. The process according to claim 1, wherein said reaction temperature if 50° to 90° C.

8. The process according to claim 1, wherein said initial concentration of said 2-alkenal is 6 to 20% by weight based on the reaction mixture.

9. The process according to claim 8, wherein said initial concentration of said 2-alkenal is 10 to 18% by weight based on the reaction mixture.

10. The process according to claim 1, wherein said reaction mixture contains from 0.5 to 10% by weight based on the reaction mixture of the acid component and its corresponding base.

11. The process according to claim 10, wherein said reaction mixture contains from 0.5 to 5% by weight based on the reaction mixture of the acid component and its corresponding base.

12. The process according to claim 1, wherein said 2-alkenal is acrolein or methacrolein.

13. The process according to claim 1, wherein said base is selected from the group consisting of alkali metal or alkaline earth metal salts, hydroxides, or carbonates.

14. A process for the preparation of 1,3-propanediol, said process comprising
   (a) forming an aqueous solution of 3-hydroxypropionaldehyde by hydrating a reaction mixture containing acrolein with water in a homogenous phase in the presence of an acid catalyst at a reaction temperature of from 20° C. to 120° C., a pressure of from 1 bar to 20 bar, and an initial concentration of said acrolein in said reaction mixture of from 3 to 30% by weight, wherein said catalyst is a dissolved acid-base buffer comprising acetic acid, propionic acid or acrylic acid as said acid and trimethylamine, triethylamine, tripropylamine or pyridine as said base;
   (b) separating unreacted acrolein from said aqueous solution of 3-hydroxypropionaldehyde;
   (c) hydrogenating said aqueous solution of 3-hydroxypropionaldehyde after step (b) with a hydrogenation catalyst to form a reaction mixture containing said 1,3-propanediol;
   (d) distilling off said acid catalyst and water from said reaction mixture containing 1,3-propanediol and recycling said acid catalyst and water to (a).

15. The process according to claim 14, wherein said acid-base buffer is propionic acid/triethylammonium propionate.

* * * * *